(12) United States Patent
Thomas (10) Patent No.: US 9,350,985 B2
(45) Date of Patent: May 24, 2016

(54) METHOD AND CIRCUITRY FOR REMOVING CIRCLING DRIFTS IN NDT/NDI MEASUREMENT DISPLAY

(71) Applicant: Andrew Thomas, Westford, MA (US)

(72) Inventor: Andrew Thomas, Westford, MA (US)

(73) Assignee: OLYMPUS NDT, INC., Waltham, MA (US)

(*) Notice: Subject to any disclaimer, the term of this patent is extended or adjusted under 35 U.S.C. 154(b) by 357 days.

(21) Appl. No.: 14/036,078

(22) Filed: Sep. 25, 2013

(65) Prior Publication Data

US 2015/0085143 A1 Mar. 26, 2015

(51) Int. Cl.
*H04N 17/00* (2006.01)
*G01N 27/90* (2006.01)

(52) U.S. Cl.
CPC ......... *H04N 17/004* (2013.01); *G01N 27/9046* (2013.01)

(58) Field of Classification Search
CPC ...... H04N 17/00; H04N 17/045; G09G 3/006
USPC .............. 348/189, 92, 95, 180, 190, 192; 324/76.11, 76.29, 76.44, 207.12; 702/35

See application file for complete search history.

(56) References Cited

U.S. PATENT DOCUMENTS

| 6,201,391 | B1 * | 3/2001 | Burkhardt | G01N 27/82 324/233 |
| 7,362,096 | B2 * | 4/2008 | Oberdier | G01D 3/036 324/209 |
| 2013/0030726 | A1 * | 1/2013 | Thomas | G01N 29/32 702/56 |
| 2013/0187643 | A1 * | 7/2013 | Lysen | G01N 27/9046 324/238 |

* cited by examiner

*Primary Examiner* — Jefferey Harold
*Assistant Examiner* — Jean W Desir (57) ABSTRACT

Disclosed is a method and an apparatus for removing circling drifts on the display of the measured eddy current or other continuous waves. The circling dot which is supposed to be a static dot can obscure information required by the operator to judge if a small defect is present. Embodiments of presently disclosed harmonic rejection filters are tunable and employed to effectively abate or eliminate signals with frequencies that are multiples of operating frequencies, resulting in the removal of the circling effects on the display.

22 Claims, 5 Drawing Sheets

METHOD AND CIRCUITRY FOR REMOVING CIRCLING DRIFTS IN NDT/NDI MEASUREMENT DISPLAY

FIELD OF INVENTION

The present invention relates generally to non-destructive testing and inspection (NDT/NDI) method and instruments, more specifically to a method and a circuitry for removing circling drifts on the display of an NDT/NDI instrument, such as an eddy current instrument.

BACKGROUND OF THE INVENTION

When using an NDT/NDI device, such as an eddy current flaw detector inspecting a test object with a large thickness, low or very low operating frequencies are required. Some instruments are designed to operate at frequencies as low as 10 Hz. The frequency at which the instrument operates is referred to as the "operating frequency". Under most testing scenarios, the instrument sends a strong excitation signal to the probe to form the eddy current in the material under test. The instrument is tasked to measure very small changes to the phase and amplitude of the signal returned to the probe as it is moved across the surface of the test object. The signal returned from the probe is amplified and sent to the detectors. Two synchronous detectors are normally used in existing practice to determine the phase angle of the received signal. The detector channel that detects the "in phase" component is referred to as the Real detector and the detector that detects the 90 degree shifted component is referred to as the Imaginary detector. Most existing methods of measuring the amplitude of an AC signal produce a DC signal with a very large ripple. Most of this ripple has a frequency twice the operating frequency and a smaller amount has the same frequency as the operating frequency. The real and imaginary detector outputs are then sent to a pair of identical filters. The filtered outputs detectors are then used for the measurement and for display.

The most common way of displaying the signals is to display a moving dot on an impedance plane displayed on a display screen. The output from the real detector and filter typically moves the dot up with increasing amplitude; the output from the imaginary detector and filter typically moves the dot to the right if the signal lags the excitation signal or to the left if the signal leads the excitation signal.

The difficulty with this method is with the filters used in existing technologies. In prior designs such as that was disclosed in U.S. Pat. No. 7,362,096, a low pass filter or a pair of low pass filters are used. Low pass filters are known to have a "roll-off" or "cut-off" frequency, the frequency above which signals are filtered out. Typical low pass filters require the unwanted signal to have a frequency several times the roll off frequency of the filter. When the low pass filter is set to a very low frequency, the instrument responds to signal changes very slowly. When the low-pass filter roll off frequency is increased to increase the instrument response, some of the AC signal leaks through the low pass filter. The leaked signals from the two low pass filters are 90 degrees from each other in phase and therefore they collectively move the dot in a circle. The problem is often referred to as "circles" or "circling dot" and a solution to it is long sought in the field of eddy current testing. The circular motion around the dot on the display where it should be stationarily located makes it very difficult to interpret the results. As a result, it hinders the inspection productivity.

The same problem and limitations are present in both analog and digital circuit designs. The same problem also exists for testing instrument of other technologies such as ultrasonic and Hall Effect testing when undesirably leaked signals of two orthogonal phases present.

Accordingly, a solution is needed to overcome the drawbacks described above and to achieve advantages of higher readability and accuracy of testing results and improved inspection productivity.

SUMMARY OF THE INVENTION

Accordingly, it is an object of the present disclosure to teach an apparatus and method that significantly reduces or eliminates the aforementioned problem of circling dot on the displays of an NDT/NDI instrument, particularly during the testing of test objects with large thickness using an eddy current instrument.

It is further an object of the present disclosure to improve measurement accuracy and operation efficiency of an NDT/NDI instrument by removing the drift causing the circling dot in the measurement result.

It is yet further an object of the present disclosure to teach a novel tunable harmonic rejection filter, and to employ the same in a signal processing circuitry to remove noise signals at predetermined frequencies which cause the circling dot.

The foregoing and other objects of the invention are realized with the use of a harmonic rejection filter to filter out signal components that cause the indicator dot to move in unwanted circle-like patterns on the display of eddy current instruments. One of the novel aspects of this invention is that the harmonic rejection filter frequency is tuned so that it very closely matches the operating frequency.

Another novel aspect is that the harmonic rejection filter has a length that is set with an effective resolution much smaller than one sample in order to decrease the limitations of box car filters to tune to the frequencies commonly used by instruments.

Yet another novel aspect of the invention is to employ adjustable sample rate reducer so that the sample frequency matches the multiples of the working frequency of a simplified version of the harmonic rejection filter.

DETAILED DESCRIPTION OF EMBODIMENTS OF THE INVENTION

Figure 1:
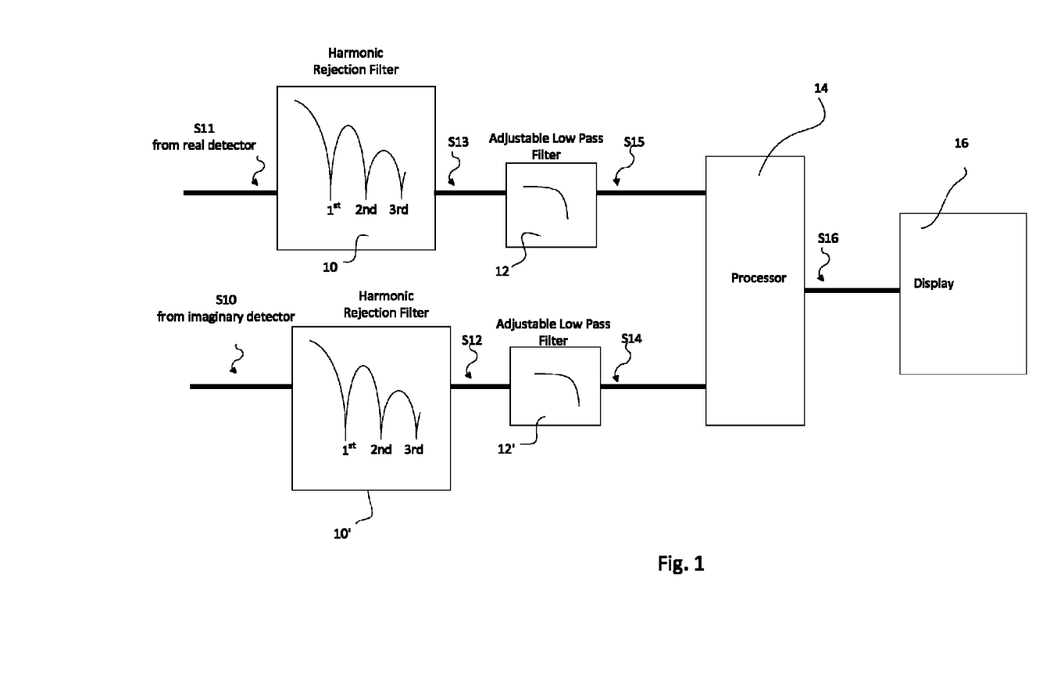
FIG. 1 is a schematic diagram of the presently disclosed circuitry, embodying harmonic rejection filters for an exemplary eddy current instrument.

As known in the art that eddy current technology usually involves detecting changes in induced eddy current response signals sensed by an eddy current probe when the probe is moved across the surface of a test object. The response signals, in their analog form, are usually processed and converted to digital signals in real and imaginary phases for subsequent digital processing. FIG. 1 is a schematic view of a digital signal processing circuitry according to the presently disclosed embodiment with the capability of abating or eliminating circling dot in the display of measurement results.

Referring to FIG. 1, the digital signal processing circuitry, according to the presently disclosed preferred embodiment, comprises two filtering channels; each embodies a harmonic rejection filer, 10 and 10' respectively, a low pass filter 12 and 12', respectively. The digital processing circuitry further comprises a data processor 14 and a display 16.

The signal from the real or "in phase" detector (not shown) is filtered through the first filter channel to processor 14 and display 16. The signal from real detector S11 needs to be filtered before it can be used to indicate the detected signal amplitude. The signal from real detector S11 is first filtered through a first harmonic rejection filter 10, which removes almost all of the signals harmonically related to the operating frequency and outputs detected real signal amplitude S13. Detected real signal amplitude S13 is then filtered through first adjustable low pass filter 12. First adjustable low pass filter 12 outputs detected real signal amplitude S15, which has had almost all of the signals harmonically related to the operating frequency removed by first harmonic rejection filter 10 and any high frequency noise removed by first adjustable low pass filter 12.

Continuing with FIG. 1, the signal from the imaginary or "out of phase" detector (not shown) is filtered through the second filter channel to processor 14 and display 16. The signal from imaginary detector S10 needs to be filtered before it can be used to indicate the detected signal amplitude. Signal from imaginary detector S10' is first filtered through second harmonic rejection filter 10'. Second harmonic rejection filter 10' removes almost all of the signals harmonically related to the operating frequency and outputs detected imaginary signal amplitude S12. Detected imaginary signal amplitude S12 is then filtered through second adjustable low pass filter 12'. Second adjustable low pass filter 12' outputs detected imaginary signal amplitude S14, which has had almost all of the signals harmonically related to the operating frequency removed by second harmonic rejection filter 10' and any high frequency noise removed by second adjustable low pass filter 12'.

Subsequently, detected real single amplitude S15 and detected imaginary single amplitude S14 are processed by processor 14, and preferably applied with an offset correction (often referred to as a "null") and a gain to calculate the position of the measurement dot. Data containing the desired image S16 is then sent out to display 16, which makes the image visible for the operator.

As can be seen in FIG. 1, the input signal data including signal data in real phase (S11) and signal data in imaginary phase (S10), and the process of receiving the input signal data, proving a harmonic rejection filtering at rejection filters 10 and 10' are preferably conducted in two parallel and identical sequences, one for filtering the data in the real phase, one for filtering the data in the imaginary phase.

It should also be noted that harmonic rejection filter 10 is not intended to replace the low pass filters 12 and 12' used by existing practice. Although the instrument is functional using only the harmonic rejection filter or the low pass filter, it is expected that in most applications, according to the present embodiment with the addition of harmonic rejection filters 10 and 10', the instrument should provide significantly better performance when the low pass filter and the Harmonic Rejection Filter are used together.

It is common for existing eddy current instruments to use two detectors and two filter channels. One channel detects the "in phase" or real component of the signal, the other detects the "out of phase" or imaginary signal component. These two signals are then filtered in identical filters and then used to position the dot on the display. The synchronous detectors used for this application out put the slow moving "DC" signal that is to be displayed plus an AC signal of twice the operating frequency that is the same magnitude as the DC signal that must be filtered out. These are separated in the filter, the DC to the display and the AC is blocked. That is how the low pass filter is intended to work. In reality some of the AC leaks through and cause the display dot to move in circles, making the smaller movements of the dot hard for the operator to detect. It is required by the operator that very small movements of the dot be visible so that small flaws in the material being inspected can be detected.

Now the challenge becomes to present a harmonic rejection filter that, working with the rest of the digital processing circuit, to serve the purpose of removing almost all of the signals harmonically related to the operating frequency and the multiples of the operating frequency.

Previous box car filters designs have a length that must be an exact integer number of samples. This limits the ability to tune the filter to match the frequency of operation. This difference between the frequency of operation and the tuned frequency of the filter will cause some of some of the harmonic energy pass through the filter.

Figure 2:
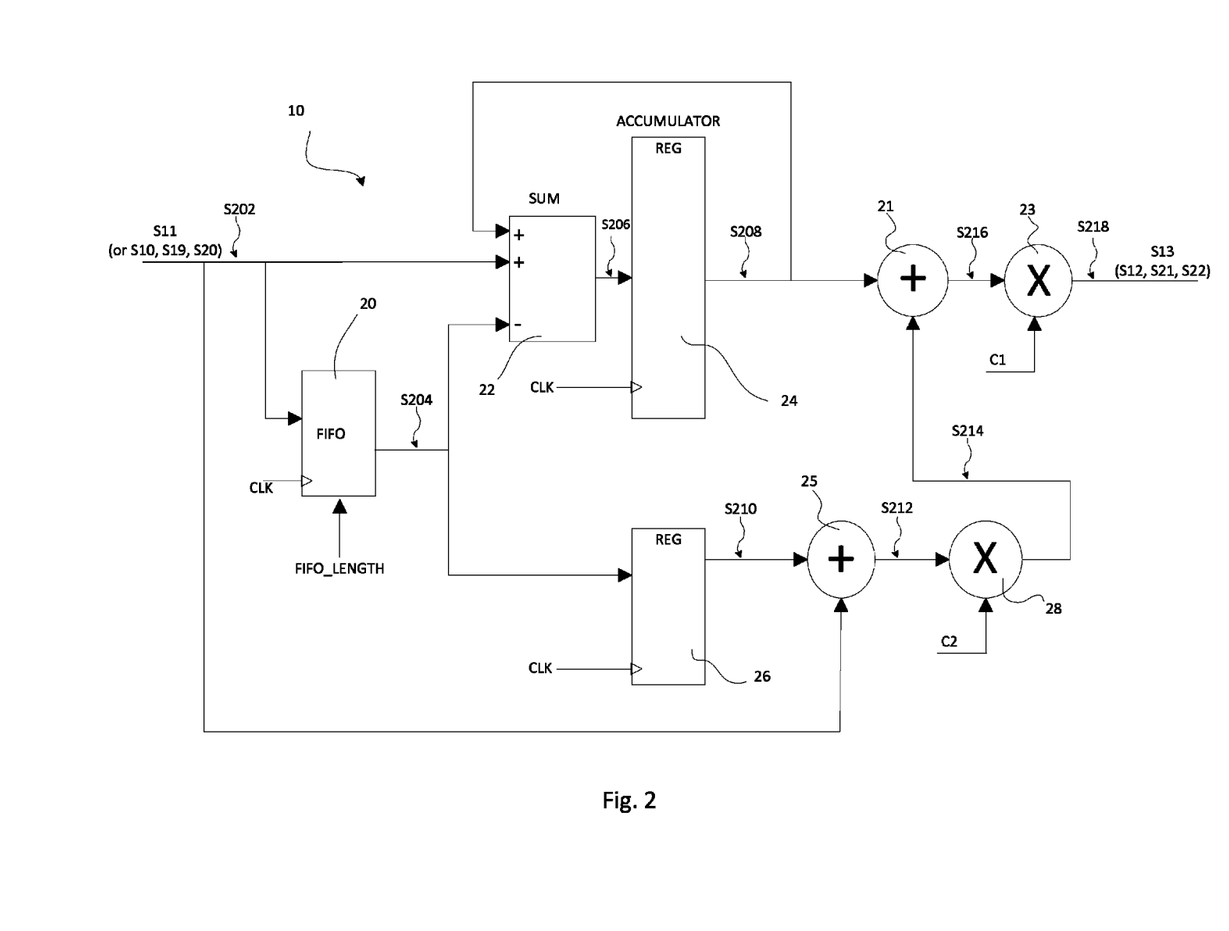
FIG. 2 is a schematic diagram providing a more detailed embodiment of the presently disclosed harmonic filters which has the ability to be tuned to frequencies that have a period that is not an integer number of sample points.

Referring now to FIG. 2, harmonic rejection filter 10 according to the preferred embodiment, further comprises a memory device 20 (in the preferred embodiment memory device 20 is of a type known as FIFO or "First In First Out"), a three input adder 22, an accumulator register 24, an oldest data point register 26, a fractional data point adder 25, a fractional data point multiplier 28, a data point adder 21 and an output scaling multiplier 23.

It is known to those skilled in the art that each FIFO has its own fixed length, herein defined as "FIFO_LENGTH". However, one can also recognize that the circuitry of harmonic rejection filter 10 as a whole has its own filter length, which is herein defined as "designed filter length", herein after as "DFL". As described in the following, the designed filter length is also programmable.

According to FIG. 2, each input data S202 is sent into harmonic rejection filter 10 and is then sent to memory device 20 to be stored, to three input adder 22, and to the fractional data point adder 25. Memory device 20 stores input data S202 for a "FIFO_LENGTH" number of clock cycles (in this implementation memory device 20 is being used as a delay) and sends out a stream of data points S204. The stream of data points that come out of memory device 20 are the same data points that entered from S202 after a delay of FIFO_LENGTH number of clock cycles. (Clock is show as CLK in FIG. 2; the data points advance through the circuit at a rate of one datum per clock cycle.) The memory 20 outputs data S204 then goes into two places; the oldest data point register 26 and three input adder 22. Three-input adder 22 adds together input data S202 and accumulator register 24's current value S208 and subtracts stream of data points S204. The sum in S206 is to be the next accumulator register 24's value on the next clock cycle. The value at the output of adder device SUM 22, signal S206 always equals the sum of all data points currently stored in the FIFO memory 20. Oldest data point register 26 stores a stream of data points S204 for one clock cycle, which then becomes the oldest data point S210. Fractional data point adder 25 then takes oldest data point S210 and adds it to input data S202 and gets sum of the newest and oldest data points S212. Fractional data point multiplier 28 then multiplies sum of the newest and oldest data points S212 by coefficient C2, which produces calculated fractional data points S214. Calculated fractional data points S214 is then added to accumulator register 24's current value S208 by data point adder 21 resulting in complete filter output S216. Output scaling multiplier 23 then multiplies complete filter output S216 by a coefficient approximately equal to C1 in order to produce output data S218, which is equal in magnitude to input data S202.

It should be noted that FIFO_LENGTH, C1 and C2 are all determined by processor 14 in response to the operator's selection of an operating frequency. Preferably, $$C1=1/DFL \qquad \text{Eq. 1}$$

$$C2=(DFL-INT(DFL))/2 \qquad \text{Eq. 2}$$

$$FIFO\_LENGTH=INT(DFL) \qquad \text{Eq. 3}$$

wherein, DFL is the designed filter length of the harmonic rejection filter, as noted above. C2 therefore is half of the decimal portion of DFL according to Eq. 2.

The physical length of harmonic rejection filter 10 (DFL) is increased by two data points beyond the setting of FIFO_LENGTH. This is because one data point that is no longer stored in FIFO 20 is now stored in the oldest data point register 26, and the immediate use of input data S202 before it is included in accumulator 24 or stored in FIFO 20.

Continuing with FIG. 2, it should be noted of the special function of the usage of a sub-circuitry 15 which embodies fractional data point adder 25, fractional data point multiplier 28 and data point adder 21. If circuitry 10 to be without sub-circuitry including components 25, 26 and 28, the physical length of the filter is the number of consecutive input data used to calculate the current output data. On each clock cycle a new input data is accepted and the oldest is lost. In concept on each clock cycle all the data points are advanced one location. On the other hand, with the addition of sub-circuitry 15, a new output data is calculated using the new data point and all the retained data points according to the new positions in the queue. This enhancement allows the effective filter length to be set to a fractional number of data points. For example if a filter length of 10.3 was desired, then C2 would be set to 0.15 and the FIFO_LENGTH set to 10. This would extend the effective filter length by 0.15 at both ends, thus the total effective length is 0.15+10+0.15=10.3. This produces a signal with the desired frequency response at the output of adder 21 as signal S216.

It can be understood by those skilled in the art that the amplitude of signal S216 is much larger than that of the input signal S202. In most implementations it is desired that the input signal S202 and the output signal S218 have equivalent amplitudes. To adjust the amplitude the signal S216 it is multiplied by coefficient C1 to provide the harmonic rejection filter (10) output signal S218. For the example length of 10.3, C1 would be set to 1/"effective filter length"=1/10.3=0.097.

As can be seen now that the function of circuitry 10 is to provide the abated or eliminated amplitude of signal S216 for any desired frequency, with enhanced precision by using C2 to adjust the filter to substantially the exact DFL, not just for the physical length of the filter.

It should be noted that coefficient C2 according to Eq. 2, can be set to a negative value; this would make a filter with an effective length that is shorter than FIFO_LENGTH. This would not represent a different filter design, only a small change in the math used to calculate the control values C2 and FIFO_LENGTH. For example an effective filter length of 10.3 could be achieved by setting FIFO_LENGTH=11 and C2=−0.35. The value of C1 would remain 1/10.3=0.097. Total effective filter length would be unchanged, but with a new equation and the same answer of −0.35+11−0.35=10.3. Simulation indicates the ideal values for C1 are limited to the range of about −0.25 to +0.25.

It should be noted that the detector output contains a $2^{nd}$ harmonic that is of the same amplitude as the desired DC signal. Harmonic rejection filter 10 produces the same DC amplitude result while reducing or abating signal amplitude at the second harmonic frequency.

Figure 3:
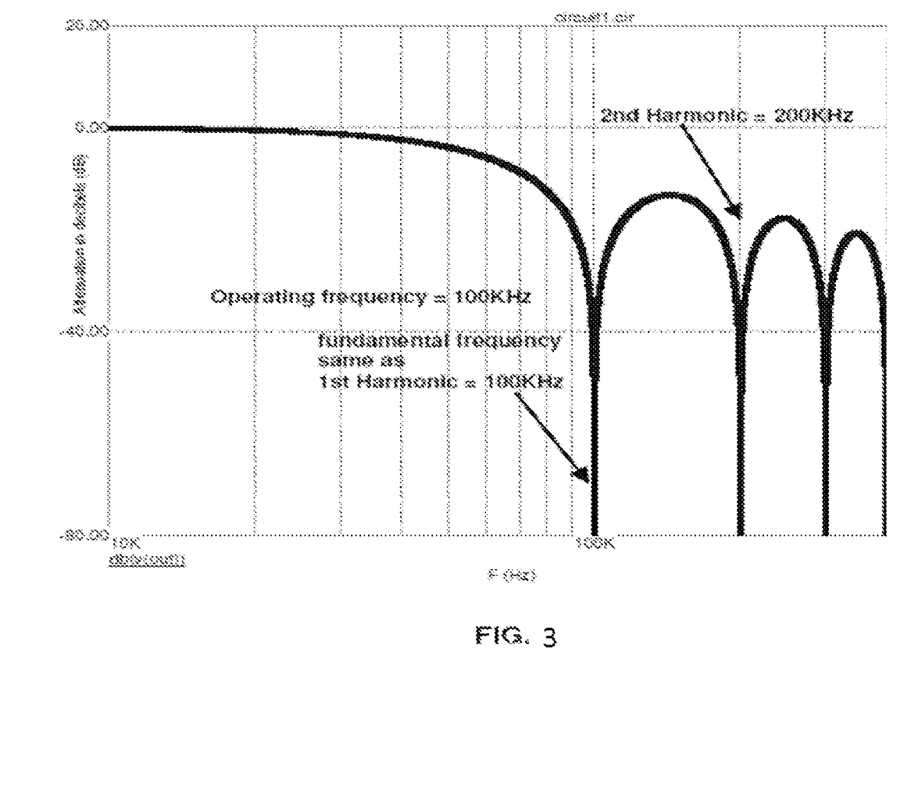
FIG. 3 is a frequency/attenuation graph of the presently disclosed harmonic rejection filter.

Referring to FIG. 3, a graph presenting the frequency response of the presently disclosed harmonic rejection filters is shown. The graph is exemplary shown under the operating frequency set to 100 KHz. Harmonic rejection filter 10 or 8 is tuned to produce signals S218 in FIGS. 2 and 3 with two notch frequencies. The first notch frequency is the same as the operating frequency of 100 KHz so as to remove any signal components with the operating frequency of 100 KHz. The second notch is tuned to the $2^{nd}$ harmonic of the operating frequency which is 200 KHz so as to remove any signal components with a frequency of 200 KHz from the detected signal before it is displayed. It should be noted that the nature of signal S11 is that it is in a Sine wave form. (It is the same for signals S10, S19 and S20). It can be understood by those skilled in the art that, shown in FIGS. 2 and 3, the operating principle of the harmonic rejection filter is that adding and subtracting all the values of evenly distributed data points for a full cycle of a Sine wave should yield zero. This is why the resultant signal of circuitry 10 has abated or eliminated amplitude at the operational frequency, and at the subsequent frequencies of N times of the operational frequency.

Figure 4:
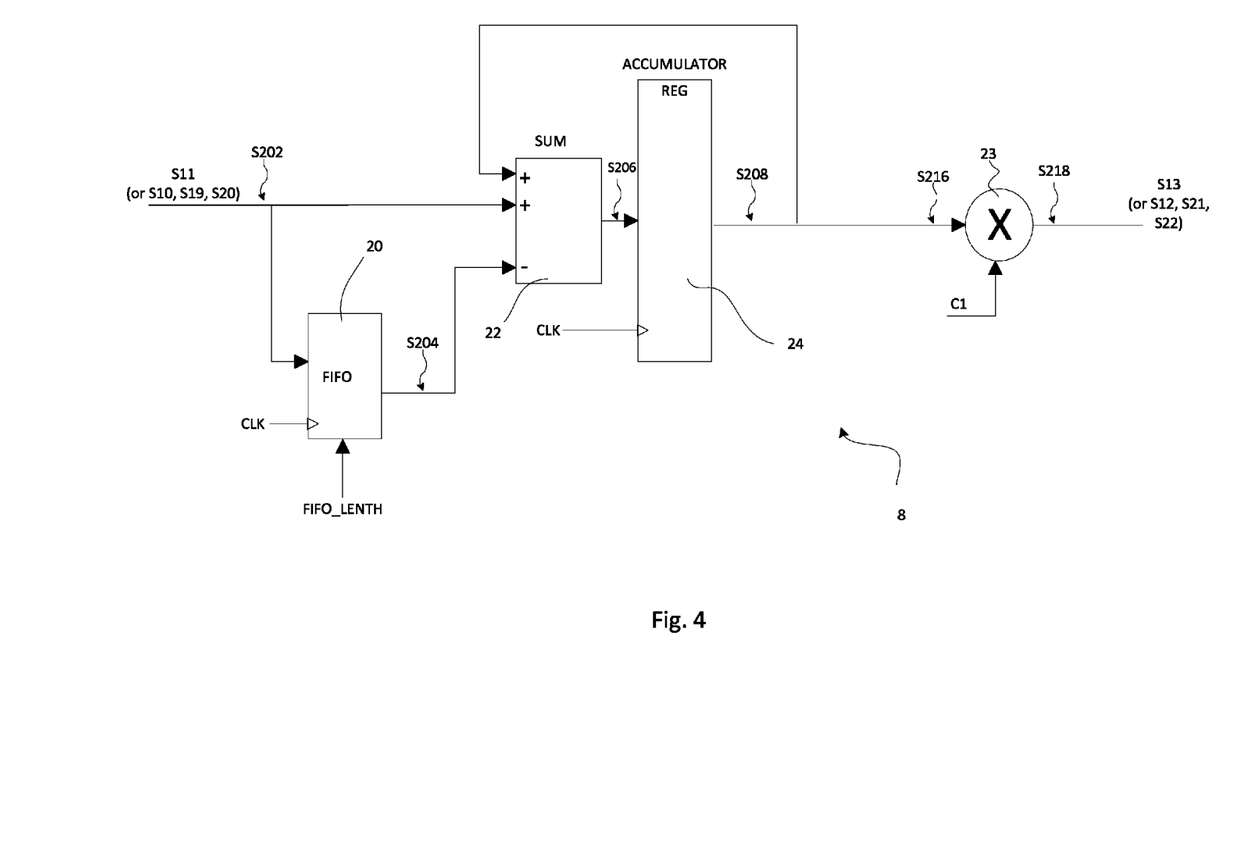
FIG. 4 is schematic diagram of alternative embodiment of the harmonic rejection filter that can only tune frequencies that have a period equal to an integer number of samples.

Continuing with FIG. 3, it should also be noted that, when C2=0 in Eq. 2, the harmonic rejection filter changes into an alternative embodiment that can be effective when the effective filter length is set exactly at an exact integer number of samples. FIG. 4 presents this alternative design of harmonic filter which is equivalent to the harmonic filter 10, but without the portion of circuitry including components 26, 25 and 28 shown in FIG. 2.

As shown in FIG. 4, similar to the harmonic frequency rejection function provided by that of filter 10, simplified harmonic filter 8 also functions to abate or eliminate signal amplitude at multiples of operational frequencies. However, this design which is equivalent circuit 10 when C2=0, is not effective when operational frequency, or the effective filter length, is not set exactly at an exact integer number of samples. It is therefore another novel aspect of the present disclosure to teach a filtering circuitry, working with the simplified embodiment of harmonic filter 8, that effectively removes signals of frequencies which are multiples of the operating frequency.

Figure 5:
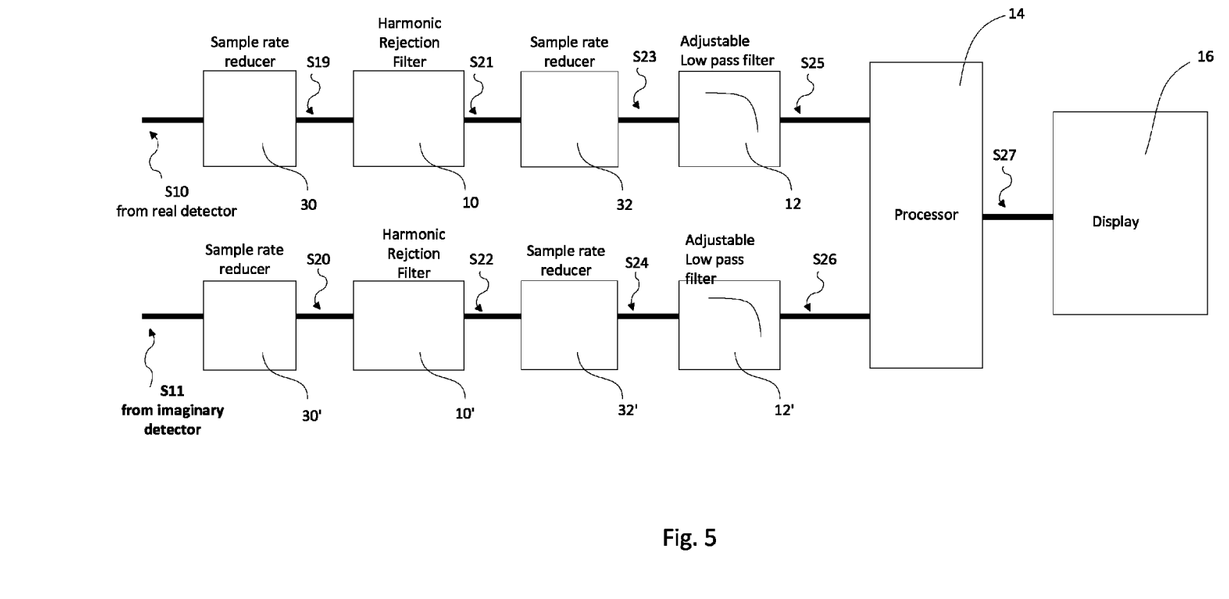
FIG. 5 is a schematic block diagram showing an alternative embodiment of a circuitry embodying the presently disclosed harmonic filters with respective sample rate reducers.

Reference now is made to FIG. 5, which presents an alternative embodiment of the digital signal processing circuitry providing function of eliminating circling dot on the impedance plane. Comparing with the digital processing circuitry presented in preferred embodiment shown in FIG. 1, two sample rate reducers are added.

As seen in FIG. 5, with signal S11 in this embodiment from the real or "in phase" detector (not shown) is sent through a filter channel to processor 14 and display 16. The filter channel comprises a first A sample rate reducer 30; first harmonic rejection filter 10, another first B sample rate reducer 32, and first adjustable low pass filter 12. Data from real detector S11 could have a high sample rate (e.g. 100 MHz) and need to be run through the first A sample rate reducer 30. The first sample rate reducer 30 takes data with a high sample rate and reduces it by taking a number of consecutive input data points and averaging them to produce each output datum S19. This is different from a typical filter in that most filters do not change the data sample rate. When the data sample rate exceeds the tuned frequency of a Harmonic rejection filter by a significant amount, the resources required to build the filter are increased and can be a burden. The first A sample rate reducer 30 reduces the data rate so that first harmonic rejection filter 10 can be implemented with a reasonable amount of resources. As a result, sampled data S19's reduced rate makes it suitable for input into first harmonic rejection filter 10. After signal S19 is filtered through first harmonic rejection filter 10, sampled data S21 has the harmonics of the operating frequency filtered out. The first B sample rate reducer 32 is then used to reduce the sample rate of sampled data S21 further before entering first adjustable low pass filter 12 as signal S23. The optimum data input rate for the low pass filter is dependent on the operator's selection of the low pass filter cutoff frequency. Low pass filter 12 output data stream S25 is then sent to processor 14 and indicates the amplitude of the real signal component of the signal received from the probe. This value changes as the operator moves the probe. Signal S25 has been filtered so that it is as pure as reasonable possible and not contain random noise and operating frequency harmonics that cause the display of circles or noise.

It should be noted that aforementioned roll-off frequency and cutoff frequency are known to those skilled in the art as basic working parameters of low pass filters.

Continuing with FIG. 5, similarly, the signal from the imaginary or "out of phase" detector (not shown) is sent through an identical filter channel to processor 14 and display 16. The lower filter channel comprises a second A sample rate reducer 30', second harmonic rejection filter 10', a second B sample rate reducer 32', and second adjustable low pass filter 12'. Data from imaginary detector S18 could have a high sample rate (e.g. 100 MHz) and need to be run through second sample rate reducer 30'. Second A sample rate reducer 30' takes data with a high sample rate and reduces it by taking a number of consecutive input data points and averaging them to produce each output datum S20. This is different from a typical filter in that most filters do not change the data sample rate. When the data sample rate exceeds the tuned frequency of a Harmonic rejection filter by a significant amount, the resources required to build the filter are increased and can be a burden. Second A sample rate reducer 30' reduces the data rate so that second harmonic rejection filter 10' can be implemented with a reasonable amount of resources. As a result sampled data S20's reduced rate makes it suitable for input into second harmonic rejection filter 10'. After signal S20 is filtered through second harmonic rejection filter 10' sampled data S22 has the harmonics of the operating frequency filtered out. The second B sample rate reducer 32' is then used to reduce the sample rate of sampled data S22 further before entering second adjustable low pass filter 12' as signal S24. The optimum data input rate for the low pass filter is dependent on the operator's selection of the low pass filter cutoff frequency. Sampled data S24 then has a reduced rate suitable for input into second adjustable low pass filter 12'. Data stream S26 is then sent to processor 14 and indicates the amplitude of the real signal component of the signal received from the probe. This value changes as the operator moves the probe. Signal S26 has been filtered so that it is as pure as reasonable possible and not contain random noise and operating frequency harmonics that cause the display of circles or noise.

Processor 14 then takes detected real single amplitude S25 and detected imaginary single amplitude S26, applies an offset (often referred to as a "null") and digital gain effect to calculate the position of the measurement dot. Data containing the desired image S27 is then sent out to display 16, which makes the image visible for the operator.

It should be noted that harmonic rejection filter 8 in its alternative embodiment shown in FIG. 4 presents a novel aspect in the present disclosure to be used in the context of circuitry shown in FIG. 5 to achieve the effect of not only eliminating signal amplitude at operation frequency, but also at multiple of operation frequencies. Under the scope of the present invention, one can make use of A sample rate reducer (30 or 30') shown in FIG. 5 in a way to adjust the frequency to be significantly close to that of exact number of samples. This effectively helps to avoid or get around the issues when operational frequency is not an exact number of data samples (fractional of data samples).

The selected operating frequency can be intentionally set with a wave period that can be measured in samples. Once the number of samples per wave is determined, filter 8 can be configured to remember said number of samples and provide an average. The advantage is that at any point in time the filter contains the data sampled from the last 360 degrees of the received signal. In theory simplified harmonic filter 8 can block all of the operating frequency and all the harmonics. This explicitly targets the very high amplitude $2^{nd}$ harmonic. Another advantage is the response speed of the instrument is not reduced.

Therefore it should be appreciated that configurations shown in alternative embodiment of harmonic rejection 8 (FIG. 4) with the combination usage of alternative circuitry shown in FIG. 5, as well as any other alternative filtering method achieving the elimination of signal amplitude at multiples of operational frequency are all covered with the scope of the present disclosure.

The forgoing description of circuits is implemented as a digital processing circuit. However, there are equivalents that could be implemented in an analog system. It is conceivable that, enlightened by the teaching of the present disclosure, one skilled in the art can device an analog circuit with the usage of, for example, tunable notch filters, to eliminate the signal amplitude right at the first harmonic frequency and harmonic frequencies of the second, third and so on. Such alternative designs are within the scope and teaching of the present disclosure, which is to treat the cause of the circling drift by removing signal amplitude at all harmonic frequencies.

It should be noted that the implementation of the circuitry can take many alternative forms. For example, harmonic filter 10 or 10' can be designed into a processing chip alone, or it can be designed together with low-pass filter 12 or 12' into one chip. In addition, two harmonic filters 10 and 10' can be implemented in one single chip with two channels, or they can be in separate chips. It should be understood that all variations of this nature are covered and enlightened by the scope of the present disclosure.

What is claimed is:

1. A circuitry configured for processing digitized measurement input data for a non-destructive testing and inspection (NDT/NDI) instrument, the instrument is configured to operate at an operating frequency, chosen from a plurality of possible operating frequencies, the digitized input data including data of the operating frequency, the circuitry comprises,
    at least one filtering channel receiving the digitized input data and producing a first set of filtered data in real phase and in imaginary phase, a data processor processing the filtered data and preparing display data containing measurement result for display, and a display unit displaying the measurement result according to the display data, wherein the at least one filtering channel including at least one first harmonic rejection filter which is configured to substantially abate amplitude of the first set of filtered data at the operating frequency and frequencies which are multiples of the operating frequency in two parallel and identical sequences, one for filtering the data in the real phase, one for filtering the data in the imaginary phase.

2. The circuitry of claim 1, wherein the at least one filtering channel including a first filtering channel for filtering the input data in real phase and a second filtering channel for filtering the input data in imaginary phase.

3. The circuitry of claim 1, wherein the filtering channel further comprising a first low pass filter.

4. The circuitry of claim 1, wherein the first harmonic rejection filter further comprises a memory component for storing a predetermined number of samples of the digitized input data, a three input adder and an accumulator register, and wherein the harmonic rejection filter has a designed filter length (DFL).

5. The circuitry of claim 4, wherein the memory component is a First-In-First-Out (FIFO) unit with a filter length of FIFO-length, and at a specific clock cycle, the digitized input data is fed to the FIFO unit and the three input adder; and, wherein the three input adder is configured to achieve a three input sum by adding together the digitized input data and the accumulator register's current value S208 at the clock cycle and subtracting data coming from the FIFO unit, and wherein the three input sum is to be the accumulator register's value on a next clock cycle immediately subsequent to the clock cycle.

6. The circuitry of claim 5, wherein the harmonic rejection filter further comprises an oldest data register, a fractional data point adder and a fractional data point multiplier.

7. The circuitry of claim 6, wherein the oldest data register is configured to receive the oldest data sample coming from the FIFO unit and the fractional data point adder is configured to achieve a fractional data point sum at the clock cycle by adding data from the oldest data register with data sample of the digitized input data, and, wherein the fractional data point multiplier multiplies the fractional data point sum with a co-efficient C2 to produce fractionally adjusted data S214.

8. The circuitry of claim 7, wherein the harmonic rejection filter further comprises a data point adder and an output data scaling multiplier.

9. The circuitry of claim 8, wherein the data point adder is configured to achieve a data point sum by adding the accumulator register's current value S208 with the fractionally adjusted data S214, wherein the data point sum is multiplied by a co-efficient C1 by the output data scaling multiplier to produce data S218 filtered by the harmonic rejection filter.

10. The circuitry of claim 9, wherein C1=1/DFL and C2=(DFL−INT(DFL))/2, or C2 is half of the decimal portion of the designed filter length DFL.

11. The circuitry of claim 5, wherein the harmonic rejection filter further comprises an output scaling multiplier which is configured to multiply the accumulator register's value with a co-efficient C1, wherein C1=1/DFL.

12. The circuitry of claim 1, wherein the at least one filtering channel further comprises at least one sample rate reducer.

13. The circuitry of claim 12, wherein at least one of the at least one sample rate reducer is configured to takes the input data with a high sample rate and reduces it by taking a number of consecutive input data points and averaging them to produce each an output with lowered sample rate.

14. A method of providing a signal filtering function for a circuitry configured for processing measurement input signal for a non-destructive testing and inspection (NDT/NDI) instrument, the instrument is configured to operate at an operating frequency, chosen from a plurality of possible operating frequencies, the method comprises the steps of, digitizing the input signal and providing digitized measurement input signal data, receiving the digitized measurement input signal data, providing a harmonic rejection filtering to abate signal data at frequencies of multiples of the operating frequency, processing the filtered signal data for display, wherein the input signal data including signal data in real phase and signal data in imaginary phase, and the steps of receiving the input signal data, providing a harmonic rejection filtering and providing harmonic rejection filtering are conducted in two parallel and identical sequences, one for filtering the data in the real phase, one for filtering the data in the imaginary phase.

15. The method of claim 14 further including a step of providing low pass filtering to remove signal data with frequency higher than a predetermined roll-off frequency and to produce filtered signal data.

16. The method of claim 14, wherein the step of providing a harmonic rejection filtering is provided by a harmonic filter with a designed filter length (DFL).

17. The method of claim 16, wherein the step of providing a harmonic rejection filtering further at a current clock cycle, comprising the steps of, providing a First-In-First-Out (FIFO) unit with a filter length of FIFO-length, and at a specific clock cycle, feeding the input signal data to the FIFO unit and producing an output data from the FIFO unit;

achieving a three input sum by adding together the input signal data, the accumulator register's current value at the clock cycle and subtracting the output data from the FIFO unit, and providing the accumulator register's value on a next clock cycle immediately subsequent to the current clock cycle.

18. The method of claim 17, wherein the step of providing harmonic rejection filtering further comprises the step of, achieving a fractional data point sum by adding data from an oldest data register with the input signal data, wherein the oldest data register receiving the oldest data sample coming from the FIFO unit;

multiplying the fractional data point sum with a co-efficient C2 to produce fractionally adjusted data S214.

19. The method of claim 18, wherein the step of harmonic rejection filtering further comprises the steps of, achieving a data point sum by adding the accumulator register's current value S208 with the fractionally adjusted data S214, multiplying the fractionally adjusted data S214 by a co-efficient C1 and thereby producing fractionally scaled harmonic rejection filtered data.

20. The method of claim 19, wherein C1=1/DFL and C2=(DFL−INT(DFL))/2.

21. The method of claim 16, wherein the step of providing harmonic filtering further comprises steps of scaling the accumulator register's value with a co-efficient C1, wherein C1=1/DFL.

22. The method of claim 14, wherein the input signal data including signal data in real phase and signal data in imaginary phase, and the steps of receiving the input signal data, providing a harmonic rejection filtering and providing a low pass filtering are conducted in two parallel and identical sequences, one for filtering the data in the real phase, one for filtering the data in the imaginary phase.

* * * * *